US 9,297,647 B2

(12) United States Patent
Knüttel

(10) Patent No.: US 9,297,647 B2
(45) Date of Patent: Mar. 29, 2016

(54) APPARATUS FOR DETECTING A 3D STRUCTURE OF AN OBJECT

(71) Applicant: Voco GmbH, Cuxhaven (DE)

(72) Inventor: Alexander Knüttel, Viernheim (DE)

(73) Assignee: Voco GmbH, Cuxhaven (DE)

( * ) Notice: Subject to any disclaimer, the term of this patent is extended or adjusted under 35 U.S.C. 154(b) by 0 days.

(21) Appl. No.: 14/259,942

(22) Filed: Apr. 23, 2014

(65) Prior Publication Data

US 2014/0320865 A1    Oct. 30, 2014

(30) Foreign Application Priority Data

Apr. 25, 2013    (EP) .................................. 13 165 409

(51) Int. Cl.
*G01B 9/021*    (2006.01)
*G01B 11/24*    (2006.01)
(Continued)

(52) U.S. Cl.
CPC ........ *G01B 11/2441* (2013.01); *G01B 9/02001* (2013.01); *G01B 9/02007* (2013.01);
(Continued)

(58) Field of Classification Search
CPC ........... G01B 11/2441; G01B 9/02001; G01B 9/02007; G01B 9/02032; G01B 9/02047; G01B 9/02067; G01S 7/4815; G01S 7/36; G03H 1/0005; G03H 1/0443; G03H 1/0465; G03H 1/0486; G03H 1/265; G03H 1/211; G03H 1/453; G03H 1/32; G03H 2001/0033; G03H 2001/0445; G03H 2001/0491; G01D 5/35312
USPC ....................................................... 356/457
See application file for complete search history.

(56) References Cited

U.S. PATENT DOCUMENTS 3,541,238 A * 11/1970 Enloe et al. ..................... 348/40
4,140,373 A *  2/1979 Rull ................................ 380/54
(Continued)

FOREIGN PATENT DOCUMENTS

EP        0 498 575 A2     8/1992
WO    WO 2004/094942 A2    11/2004

OTHER PUBLICATIONS

Calabuig et al., "Superesolution in digital holographic microscopy," 2011 10th Euro-American Workshop, IEEE, Jun. 19, 2011, pp. 1-3.
(Continued)

*Primary Examiner* — Tarifur Chowdhury
*Assistant Examiner* — Jonathon Cook
(74) *Attorney, Agent, or Firm* — Bose McKinney & Evans LLP

(57) ABSTRACT

An apparatus for detecting a 3D structure of an object. The apparatus has first and second laser emitters which generate laser radiation having first and second wavelengths, respectively, the first wavelength being different from the second wavelength. Optical devices are disclosed, including a beam splitter, which splits the laser radiation of the laser emitters in each case into a reference radiation and an illuminating radiation. The illuminating radiation impinges upon the object to be measured, is reflected by the object as object radiation and interferes with the reference radiation. A detector receives the interference patterns. The laser emitters are located such that the illuminating radiation of the first and second laser emitters impinge upon the object at different angles of incidence. Also discussed is a measuring device which measures the two wavelengths of the laser radiation of the laser emitters and influences the recording of the interference patterns.

18 Claims, 6 Drawing Sheets

(51) Int. Cl.
*G01B 9/02* (2006.01)
*G03H 1/00* (2006.01)
*G01S 17/36* (2006.01)
*G01S 7/481* (2006.01)
*G03H 1/04* (2006.01)
*A61B 6/14* (2006.01)
*G01N 21/21* (2006.01)
*G01N 21/45* (2006.01)
*G02B 21/36* (2006.01)
*G02B 5/32* (2006.01)
*G03H 1/26* (2006.01)
*G03H 1/32* (2006.01)
*G03H 1/02* (2006.01)

(52) U.S. Cl.
CPC ........ *G01B9/02027* (2013.01); *G01B 9/02032* (2013.01); *G01B 9/02047* (2013.01); *G01B 9/02067* (2013.01); *G01S 7/4815* (2013.01); *G01S 17/36* (2013.01); *G03H 1/0005* (2013.01); *G03H 1/0443* (2013.01); *G03H 1/0465* (2013.01); *G03H 1/0486* (2013.01); *G03H 1/265* (2013.01); *A61B 6/145* (2013.01); *G01N 21/211* (2013.01); *G01N 21/453* (2013.01); *G01N 2021/213* (2013.01); *G02B 5/32* (2013.01); *G02B 21/367* (2013.01); *G03H 1/2645* (2013.01); *G03H 1/32* (2013.01); *G03H 2001/0033* (2013.01); *G03H 2001/0212* (2013.01); *G03H 2001/046* (2013.01); *G03H 2001/0445* (2013.01); *G03H 2001/0491* (2013.01); *G03H 2001/266* (2013.01); *G03H 2210/63* (2013.01); *G03H 2222/13* (2013.01); *G03H 2222/16* (2013.01); *G03H 2222/17* (2013.01); *G03H 2222/31* (2013.01); *G03H 2222/34* (2013.01); *G03H 2222/35* (2013.01); *G03H 2223/19* (2013.01); *G03H 2223/22* (2013.01); *G03H 2223/23* (2013.01)

(56) References Cited

U.S. PATENT DOCUMENTS

| 4,583,228 | A | 4/1986 | Brown et al. |
| 6,809,845 | B1 | 10/2004 | Kim et al. |
| 8,068,235 | B1 * | 11/2011 | Marron et al. ................ 356/512 |

OTHER PUBLICATIONS

Pedrini et al., "Digital holographic interferometry for investigations in biomechanics," Proceedings of SPIE, Feb. 14, 2005, pp. 325-332.
Chen et al., "Overview of three-dimensional shape measurement using optical methods," Optical Engineering, Jan. 2000, pp. 1-13.
Schmit et al., "Surface Profilers, Multiple Wavelength, and White Light Intereferometry," Optical Shop Testing, Nov. 2, 2006, pp. 667-755.

* cited by examiner

APPARATUS FOR DETECTING A 3D STRUCTURE OF AN OBJECT

RELATED APPLICATIONS

This application claims priority to EP 13 165 409.7, filed Apr. 25, 2013, which is hereby incorporated herein by reference in its entirety.

BACKGROUND

The present invention relates to an apparatus for detecting a three-dimensional structure of an object. Apparatuses for detecting 3D structures are used, for example, in industry for quality assurance. Processed surfaces can thus be examined for their quality, for example, for adherence to dimensional accuracy and/or for adherence to a predefined roughness. Furthermore, with such apparatuses it is also possible to digitally detect and three-dimensionally map entire objects.

Such an apparatus is known from U.S. Pat. No. 6,809,845 B1. This operates according to the principle of holography. Two laser beams having different wavelengths are generated by means of two lasers. Each laser beam is split into an object beam, which impinges upon an object to be measured, and a reference beam. The object beam reflected from the object and the appurtenant reference beam of one wavelength are combined and interfere with one another, the phase relationships between the two beams being recorded. A three-dimensional model of the reflected surface of the object can be created with the aid of the difference between the phase relationships produced by the laser beam having a first wavelength and the phase relationships produced by the laser beam having a second wavelength. In addition to the lasers, an Nd:YAG laser (neodymium-doped yttrium aluminum garnet laser) and an HeNe laser (helium neon laser), the apparatus comprises a plurality of mirrors, beam splitters, filters, and apertures. The required space requirement of the apparatus is large.

U.S. Pat. No. 8,068,235 B1 also discloses an apparatus for the three-dimensional detection of surface structures. Two laser sources generate a laser beam. Parts of these laser beams are combined into a composite beam, which impinges upon the object to be measured. It is then reflected by the object and detected by a camera. The remaining parts of the emitted laser beams impinge as reference beams having different angles of incidence on the camera. Since the laser beams are partially combined via beam splitters, the apparatus has an increased space requirement.

In both patent specifications, light of two or more wavelengths impinges upon the object at identical angles. This causes so-called speckle noise because as a result of the wave nature of the light in the backscattered light of a somewhat rough surface object, zones of so-called constructive (light) and destructive (dark) interference occur. The object thereby appears "granular" for the observer, which is designated as speckle or speckle noise.

SUMMARY

The present invention provides a compact apparatus for detecting a 3D structure of an object as well as for minimizing the speckle noise.

In one embodiment, the apparatus comprises a measuring device which measures the two wavelengths of the laser radiation of the laser emitters. The measuring device influences the recordings of the interference patterns by the detector. Perturbing influences such as, for example, temperature variations can have the result that the laser emitters generate radiation having fluctuating wavelengths. With the aid of the measuring device, it is ensured that the wavelengths of the laser radiation generated by the laser emitters and the time behavior of the wavelengths are known exactly when evaluating the interference patterns.

Optionally, the measuring device measures the time behavior of the wavelengths of the laser radiation of the laser emitters, where a control device actuates the detector in the case of substantially constant wavelengths and triggers a recording of the interference patterns.

This therefore means that the apparatus optionally comprises a measuring device which allows the time behavior of the wavelengths of the laser radiation of the laser emitters to be measured and that the measuring device is optionally connected to a control device, which is suitable for actuating the detector in the case of substantially constant wavelengths and for triggering a recording of the interference patterns.

During a recording of the interference patterns by the detector, it is advantageous if the time behavior of the wavelengths is substantially constant. In the context of this disclosure, the term substantially constant wavelengths is understood to be wavelength fluctuations in the range of $10^{-6}$ and $10^{-7}$ times the emitted wavelength, i.e., in the range of about 0.1-1 pm. The interference patterns are recorded with an exposure time of preferably 10-100 μs. The short exposure time ensures that even with moderately moving objects the phase-sensitive recording is not blurred.

It is also feasible that the apparatus has a regulating device which, depending on the measurement results of the measuring device, regulates the laser emitters in such a manner that the wavelengths of the emitted laser radiation are substantially constant.

The laser emitters are located in such a manner that the illuminating radiation of the first laser emitter and the illuminating radiation of the second laser emitter impinge upon the object at different angles of incidence. Preferably the illuminating radiation of the respective laser emitter impinges upon the object at a relatively small angle of incidence. For example, with two laser emitters, the typical angle of incidence is about 0.11°. In the context of this disclosure, it was identified that advantageously when using more than two laser emitters—i.e., for example, 8—the illuminating radiation impinges upon the object at angles of incidence of at most 1°, preferably of about 0.8°. Larger angles of incidence of the illuminating radiation are also feasible.

The laser emitters can emit laser radiation having a total power of at least 100 mW, where the total power depends strongly on the exposure time.

The term illuminating radiation is understood in the context of this disclosure as the part of the emitted laser radiation, which impinges upon the object to be measured. The term object radiation designates the illuminating radiation reflected at the object. The reference radiation is the part of the emitted laser radiation which interferes with the object radiation unchanged as reference and impinges upon the detector.

In the context of this disclosure, it was identified that the apparatus according to this disclosure can also be used in the area of the human mouth. In particular, it is feasible to use the apparatus for detecting surfaces and objects in the inner mouth region, for example, as a dental scanner. In order to meet these requirements, the apparatus preferably has corresponding dimensions, which enable at least partial insertion of the apparatus into the inner mouth region.

It is expedient to configure the measuring device as a Fabry Perot interferometer. A Fabry Perot interferometer is generally known from the prior art. In the present case, a resonator of the Fabry Perot interferometer comprises two glass plates, on which mirrors are vapor-deposited in each case. Depending on the resonance conditions of the resonator, the laser radiation having specific wavelengths is transmitted through the vapor-deposited mirrors and in the present case, detected by a detector array. With the aid of the Fabry Perot interferometer, it is possible to exactly measure the wavelengths at which the respective laser emitters emit laser radiation, in a specific wavelength range. The Fabry Perot interferometer requires a certain basic stability of the wavelengths of the laser radiation emitted by the laser emitters. However, the present-day laser emitters are capable of providing such basic stability.

The first laser emitter and the second laser emitter can be located on a common emitter chip spaced apart from one another. For example, the laser emitters can be configured as multilaser diodes. The individual laser emitters can be located at a distance of at most 0.5 mm, preferably at a distance of at most 0.2 mm, especially preferably at a distance of at most 0.1 mm from one another.

Due to such small distances, multiple emitters are possible in a very narrow installation space. A plurality of emitters form a wavelength group, by means of which 3D surface information of an object and information about the depth of individual object points on the object (surface points on the object) can be detected. Two or more wavelength groups can also be located on the same chip in order to implement a reduction in speckle.

The apparatus advantageously comprises at most thirty two laser emitters, where preferably at most sixteen laser emitters are located on one emitter chip in each case. For example, all sixteen laser emitters located on one emitter chip each emit laser radiation having a different wavelength. All sixteen laser emitters form a wavelength group which can be assigned a central wavelength. In the context of this disclosure, the central wavelength is understood as the mean of all the wavelengths emitted by laser emitters of one wavelength group.

However, it is also feasible to position the sixteen laser emitters in four rows of four laser emitters each adjacent to one another on an emitter chip. Each row having four laser emitters each forms a wavelength group, which can be assigned a central wavelength. Each of the laser emitters of one wavelength group emits laser radiation having a different wavelength. The individual rows, i.e., the different wavelength groups, preferably agree in their central wavelengths.

A central wavelength can preferably be between 750 and 850 nm, in particular about 800 nm. Central wavelengths around 950 nm or even 1300 nm are also possible. Central wavelengths in the visible spectral range are also feasible, although this is technologically demanding to achieve.

Further configurations are feasible, where preferably one, two, or four wavelength groups are located on one emitter chip. The number of laser emitters in one wavelength group can vary and is not fixed at four, sixteen, or thirty two laser emitters. Also the arrangement of the emitters in relation to the individual wavelengths is not necessarily monotonically ascending or descending but can also be "random". Likewise, the number of groups on an emitter chip can differ from the number described.

It is advantageous to locate a plurality of wavelength groups on one emitter chip adjacent to one another since then a reduction in speckle can be achieved. A speckle pattern is formed by reflection of the laser radiation at an uneven surface of an object, the configuration whereof is strongly dependent on the angle of incidence of the illuminating radiation on the object and makes object identification difficult. If a plurality of wavelength groups are located adjacent to one another on an emitter chip, a larger angular spectrum with regard to the angle of incidence of the illuminating radiation is produced. For each wavelength group the depth information of the same illuminated object points is then detected at different mean angles of incidence. The mean angle of incidence is understood as the angle of incidence averaged over the angles of incidence of one wavelength group. An averaging of the depth information over the wavelength groups brings about a reduction in the influence of the speckle pattern.

If a reduction in speckle is to be accomplished, it is advantageous if the different wavelength groups agree in their central wavelengths. The expenditure in the subsequent evaluation of the interference patterns is thereby kept low. However, it is also feasible to achieve a reduction in speckle if the individual wavelength groups emit laser radiation having different central wavelengths. If the central wavelengths of the wavelength groups differ from one another, they lie close to one another, i.e., the central wavelengths differ by about 50-100 nm.

It is understood that two or more emitter chips with respectively one or more wavelength groups can be used, where the central wavelengths can agree or differ.

It is expressly pointed out that the present teachings are not limited to a number of thirty two laser emitters. The configuration with a total of thirty two laser emitters divided into two emitter chips is merely one embodiment. It is feasible to use far more than a total of thirty two laser emitters, preferably divided into a plurality of emitter chips/wavelength groups. The higher the number of wavelength groups, the better can resulting signal noise be suppressed during the evaluation of the interference patterns. The number of laser emitters used and wavelength groups is only limited by the size/pixel density of the detector and the selected illumination field on the object and the available computing power for the evaluation of the interference patterns.

One of the optical devices is configured to reflect the reference radiation in such a manner that the reference radiation of the individual laser emitters impinges upon the detector at different angles of incidence. Preferably reference radiation and object radiation of one wavelength impinge upon the detector with different angles of incidence. For example, the object radiation which was reflected at an object point of the object to be investigated impinges upon the detector at the same angle of incidence regardless of its wavelength. In this context, a minimum roughness of the surface structure of the object is assumed. In the case of an ideally smooth object, different relationships are obtained for the object radiation.

The beam paths of reference and illuminating radiation are partially superposed so that reference radiation and object radiation of one wavelength, i.e., from the same laser emitter, interfere with one another. An interference pattern per emitted wavelength is formed so that from all wavelength-dependent interference patterns, for example, in a processing device, the position of the object point on the surface of the object and the position of the object point in the depth is determined by means of a Fourier transformation or a Fresnel transformation.

In an optional embodiment, at least one of the optical devices is a hologram. The hologram deflects the illuminating radiation in such a manner that it impinges upon the object as an illuminating strip. For example, the hologram is executed as a micro-hologram. If an object is to be detected, this is scanned during a relative movement between apparatus and object along a scanning direction. Preferably the illuminating strip is configured to be rectangular, where the short sides of the rectangle run parallel to the scanning direction and the long sides are aligned transversely to the scanning direction. The micro-hologram changes the numerical aperture of the illuminating radiation in such a manner that the numerical aperture along the long sides of the rectangular illuminating strip is greater than the numerical aperture along the short sides of the rectangular illuminating strip.

If, for example, a weld seam is to be detected, the profile of the weld seam predefines the scanning direction. Since the long sides of the rectangular illuminating strip run transversely to the scanning direction, the total width of the weld seam can be detected with the aid of the illuminating strip.

Since short exposure times are used for the recording of the interference patterns, regions of the weld seam recorded by the detector overlap partially. This enables height differences, for example, due to movement of the object relative to the detector or due to mechanical errors of the apparatus during detection to be compensated.

However, it is also feasible that the hologram splits the illuminating radiation and deflects it in such a manner that two illuminating strips impinge upon the object. Advantageously both illuminating strips are located along the scanning direction (short side). This enables operation of the apparatus according to this disclosure as a hand scanner. Since two illuminating strips are used, possible relative movements, in particular rotational relative movements of the apparatus relative to the object, can be detected and taken into account in the evaluation. It is understood that the hologram can split and deflect the illuminating radiation in such a manner that more than two illuminating strips impinge upon the object.

Advantageously at least one of the optical devices is a micro-optic array. The micro-optic array is a combination of different optical components such as, for example, lenses, beam splitters, circulators and/or holograms which are located very compactly. The micro-optic array is preferably located in the beam path directly behind the laser emitters.

It is expedient that the micro-optic array comprises the beam splitter which splits the laser radiation of the laser emitter into the reference radiation and the illuminating radiation. Preferably the reference and illuminating radiation run at least partially overlapping. Consequently a particularly compact structure of the optics of the apparatus is possible.

Preferably the micro-optic array comprises a polarizer and/or circulator in order to polarize the illuminating radiation and/or the reference radiation. Preferably the reference radiation is polarized relative to the illuminating radiation such that the polarization plane is turned by 90 degrees with the aid of a polarizer and/or circulator. The polarization of the illuminating radiation on the other hand is not influenced. This is particularly advantageous if a polarizing beam splitter is located in the beam path after the micro-optic array, which for example transmits laser radiation of a first polarization, in particular the reference radiation and reflects laser radiation having a second polarization, in particular the illuminating radiation. It is also feasible to rotate the illuminating radiation with the aid of the polarizer and/or circulator by 90° and to leave the reference radiation uninfluenced.

The micro-optic array can also comprise a hologram. The requirements on the accuracy of lenses located in the beam path are thereby reduced. This reduces the costs incurred during manufacture of the apparatus.

The hologram in the micro-optic array preferably also has the effect that the reference and illuminating radiation in each case leaves the micro-optic array with a different numerical aperture. For example, the reference radiation has a high numerical aperture whereas the illuminating radiation leaves the micro-optic array at least along the short sides of the rectangular illuminating strip with a much smaller numerical aperture. Furthermore, with the aid of a hologram it is easily possible to produce a plurality of illuminating strips, for example, two illuminating strips.

Optionally one of the optical devices is configured as a chromatically dispersive lens. Preferably the chromatically dispersive lens is located in the beam path of the object radiation, i.e., in the beam direction after reflection of the illuminating radiation at the object. The expenditure of the Fourier or Fresnel transformation for the evaluation of the interference patterns can thereby be reduced.

A further embodiment of this disclosure is characterized in that the apparatus comprises two emitter chips and two detectors, where the laser radiation having a first central wavelength of the laser emitted located on the one emitter chip impinges upon the one detector and the laser radiation of a second central wavelength of the laser emitter located on the other emitter chip impinges upon the other detector. If, for example, two emitter chips having different central wavelengths are used, the individual laser radiations can be split, for example, by means of beam splitters which transmit or reflect the laser radiation depending on its central wavelengths such that laser radiation having the first central wavelength is incident on a first detector and the laser radiation having a second central wavelength is incident on a second detector.

Advantageously the apparatus comprises a measuring unit for measurement of the thickness of a layer located on the object. Consequently, in addition to the surface of the object, the thickness of a layer possibly present on the object can also be detected. If the apparatus is used as a dental scanner, the thickness of gums on a tooth can be measured. For example, such a layer thickness measurement can be implemented with the apparatus according to this disclosure without additional components. Preferably the measuring unit is configured as part of the processing device. Not only one but also a plurality of surfaces, for example, two or three surfaces, can be detected with the aid of the phase information from the interference patterns of a plurality of wavelengths. It is fundamentally the case that the more wavelengths in the wavelength group, the more reliably one or a plurality of additional surfaces are detected. Preferably two surfaces are detected by means of the apparatus and set in a relationship to one another. The outer surfaces of a layer located on the object is detected as the first surface and the surface of the object on which the layer to be measured is located, is detected as the second surface. The distance difference of the two surfaces, knowing the refractive index, yields the layer thickness, for example, the thickness of the gums.

A likewise exemplary embodiment is characterized in that the measuring unit comprises a white light point sensor which implements the principle of frequency-scanning interferometry. The principle of frequency-scanning interferometry is known from the prior art. Alternatively other methods for this measuring unit are also feasible. Preferably the white light point sensor comprises a light source which generates light having a broad spectrum, preferably around a central wavelength of 1300 nm and a width of the spectrum between 10 and 100 nm. Particularly scattering layers, for example, the gum, can be measured directly with the aid of the white light point sensor having a central wavelength of 1300 nm. After measuring the gum thickness, this is then related to the surface of the gum which was only detected with the apparatus according to this disclosure without the measuring unit. It is thereby possible to determine the 3D tooth surface below the gum.

The measuring unit can also be configured, based on the principle of ellipsometry, to determine the thickness of the layer located on the object. The principle of ellipsometry is also known from the prior art. Very thin layers, i.e., between about 0.01 µm and 1 µm can be measured with the aid of the ellipsometric approach. To this end, use can be made of the fact that different emitters sit at different lateral positions on the multi-emitter chip and can thus emit light at different angles onto the object. Together with fixedly adjusted polarizers at individual emitters in the illuminating radiation and/or fixedly adjusted analyzers (polarizers) at different places in the object radiation, it is possible to determine a thin coating thickness from the sum of all the information. At the same time, the complete 3D surface information of the object is available according to the procedure described above.

According to this disclosure, an additional optics can be configured so that light is incident on the object at a very flat angle, which is known to significantly increase the sensitivity for thin coatings in the ellipsometric approach.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DETAILED DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1A:
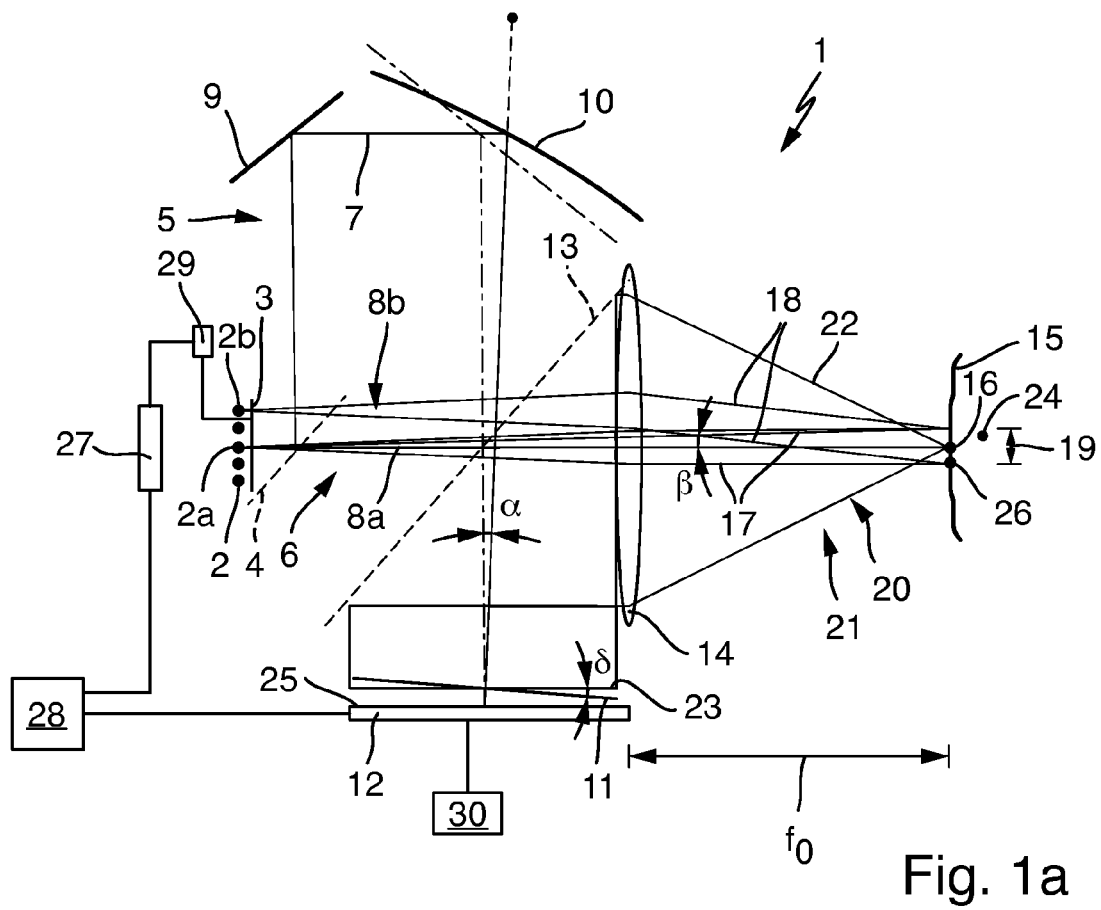
FIG. 1a shows schematically an apparatus according to a first embodiment in a Mach Zehnder setup.

FIG. 1a shows a first embodiment of an apparatus 1 according to a Mach-Zehnder setup comprising a plurality of laser emitters 2, inter alia comprising a first laser emitter 2a and a second laser emitter 2b. The laser emitters 2 are located on an emitter chip 3. They preferably have a distance of less than or equal to 1 mm to less than 0.1 mm with respect to one another. They are configured as multilaser diodes.

In FIG. 1a five laser emitters 2 which are located on the emitter chip 3 can be seen as an example. However, it is also feasible to position up to thirty two or more laser emitters 2 on an emitter chip 3.

Each laser emitter 2 emits laser radiation having a single wavelength. The wavelengths of the individual laser emitters 2 differ so that each laser emitter 2 emits laser radiation having a different wavelength. Preferably the wavelengths of the laser radiation of two adjacent laser emitters 2 differ only slightly, for example, by 1 nm. In the arrangement of 8 or 16 laser emitters 2 on an emitter chip 3, this means a spectral width of 8 or 16 nm.

The apparatus 1 comprises an optical device configured as a first beam splitter 4, which splits the laser radiation of the laser emitters 2 in each case into reference radiation 5 and illuminating radiation 6. The first beam splitter 4 can be a partially transmitting mirror, which reflects the reference radiation 5 and transmits the illuminating radiation 6.

In FIG. 1a the reference radiation 5 is shown as an example in the form of a reference beam 7 of the first laser emitter 2a located on the emitter chip 3. The illuminating radiation 6 is also shown for the first laser emitter 2a of the emitter chip 3 in the form of an illuminating beam 8a and for the second laser emitter 2b in the form of an illuminating beam 8b.

After the reference beam 7 has been reflected at the first beam splitter 4, on its further path it impinges upon an optical device configured as mirror 9 and upon a further optical device, which is designed as parabolic mirror 10. The mirror 9 and the parabolic mirror 10 reflect the reference radiation 5 in such a manner that on the one hand, it leaves the mirror 10 almost collimated and on the other hand, impinges upon a detector 12 as plane wave 11 at a reference angle of incidence α different from zero. The detector 12 is preferably configured as a high-resolution 2D surface sensor.

The mirror 9 and the parabolic mirror 10 are configured to reflect the reference radiation 5 of the individual laser emitters 2 in such a manner that the reference radiation 5 having different wavelengths, i.e., coming from different laser emitters 2, impinges upon the detector 12 at different reference angles of incidence α. In FIG. 1 the parabolic mirror 10 is shown in two different positions, once as a dashed line and once as a continuous line. The reference angle of incidence α of the reference radiation 5 can be influenced by positioning of the parabolic mirror 10.

An optical device configured as a second beam splitter 13 is located between the parabolic mirror 10 and the detector 12, which allows the reference beam 7 to pass somewhat attenuated.

After the first beam splitter 4, the illuminating beams 8a, 8b are transmitted slightly attenuated by the second main beam splitter 13 and impinge upon an optical device configured as lens 14. The lens 14 guides the illuminating beams 8a, 8b shown as an example onto an object 15 with an object point 16. The object point 16 ideally lies at the focus $f_0$ of the lens 14 or in a focal zone around the focus $f_0$. The object 15 can also then still be detected three-dimensionally if the object point 16 is located outside the focal zone.

The extension of a focal zone of the lens 14 along the optic axis around the focal point of the lens 14 (in FIG. 1a the object point 16) is dependent on the wavelength of the laser radiation transmitted by the lens 14 and on the numerical aperture of the lens 14. Assuming in the present case a numerical aperture of the lens 14 of about 0.2, the extension of the focal zone, beginning at the focal point of the lens 14 along the optic axis in the direction of the object is about +/−15 µm.

The illuminating beam 8a emitted by a laser emitter 2 as slightly spherical is transformed into a plane wave with the aid of the lens 14. In FIG. 1 this can be identified at beam edges 17 of the illuminating beam 8a, which run parallel to one another after the lens 14. The illuminating beam 8a impinges upon the object 15 as an almost plane wave and approximately at right angles, i.e., with an angle of incidence of about 0 degrees.

Upon passage of the illuminating beam 8b through the lens 14, in contrast to the illuminating beam 8a, not only the transformation into a plane wave takes place. The illuminating beam 8b is additionally deflected by the lens 14 such that it impinges upon the object 15 at an angle of incidence $\beta$, which differs from the angle of incidence of the illuminating beam 8a. As a result of the different arrangement of the laser emitters 2 relative to the lens 14, the illuminating radiation 5 of the individual laser emitters 2 is incident on the object 15 at different angles of incidence $\beta$. Preferably all the illuminating beams 8a, 8b of the individual laser emitters 2 impinge upon the object 15 in a rectangular illuminating strip 19.

It is understood that the object 15 has a finite number of object points 16 which all reflect the laser radiation. Hereafter the reflection of an illuminating beam 8a, 8b will be explained as an example for selected object points, inter alia at the object point 16, and the further beam path in the direction of the detector 12. The illuminating beams 8a, 8b reflected at the object 15 or the illuminating radiation 6 reflected at an object 15 are hereafter designated as object beam 20 or object radiation 21.

Regardless of the angle of incidence $\beta$ of an illuminating beam 8a, 8b, this is reflected as object beam 20 having edge beams 22 in the form of a spherical wave from the object point 16. The object beam 20 impinges upon the lens 14 and is transformed by this into an almost plane wave 23. This applies for the case that the object point 16 lies inside the focal zone described above or, as shown in FIG. 1, at the focal point $f_0$ of the lens 14. If an object point 24 is located outside the focal zone, an object beam 20 emitted from the object point 24 is transformed into a slightly curved wave by means of the lens 14.

The object beam 20 is incident on the second beam splitter 13, which then reflects the object beam 20 in such a manner that this impinges at an angle of incidence $\gamma$ of about zero degrees, i.e., at an angle of 90° to a detector surface 25 of the detector 12, upon this detector surface. The object beam 20 as plane wave 23 is shown as a horizontal line in FIG. 1a, which runs parallel to the detector surface 25.

The angle of incidence $\gamma$ of the object beam 20 depends on the position of the object point 16, 24. If this, like the object point 16 in FIG. 1, lies on the optic axis of the lens 14, the object beam 20 then impinges, as already described, at angle of incidence $\gamma$ of 0° on the detector surface 25. A reflection at another object point, for example, at the object point 26, results in an angle of incidence $\gamma$ different from zero on incidence on the detector surface 25.

Whereas the object beam 20 impinges upon the detector surface 25 at the angle of incidence $\gamma$, the reference beam 7 is incident on the detector surface 25 at the reference angle of incidence $\alpha$. The reference angle of incidence $\alpha$ and the angle of incidence $\gamma$ differ by a difference angle $\delta$, which is different from zero.

Since the reference beam 7 and the object beam 20 of the same wavelength encounter each other after the second beam splitter 13 on their path in the direction of the detector surface 25, they interfere with one another. As a result of this interference, an interference pattern of a specific spatial frequency is formed as a function of the difference angle $\delta$, which is recorded with the aid of the detector 12. A spatial frequency is obtained through the (quasi)-sinusoidal oscillation of the signal amplitudes, which are formed by constructive (signal accentuation) and destructive (signal attenuation) interference of the reference radiation 5 and object radiation 21 of one wavelength.

For each object point 16, 24, 26 a different difference angle $\delta$ is formed in each case at different wavelengths since the reference angle of incidence $\alpha$ varies as a function of the positions of the laser emitters 2. The illumination area on the object 15, the number of laser emitters 2, their spacings (and therefore the reference angle of incidence $\alpha$) and the pixel condition of the 2D surface detector 12 can thus be matched to one another so that no ambiguities occur in the spatial frequencies.

A requirement for a recording of the interference patterns by the detector 12 is that the laser radiation whose interference pattern is to be recorded is emitted with substantially constant wavelength by the respective laser emitters 2. For this purpose, the apparatus 1 preferably has a measuring device which is configured as a Fabry Perot interferometer 27. The Fabry Perot interferometer 27 is known from the prior art and enables the wavelengths of the laser radiation emitted by the laser emitters 2 to be measured continuously. The Fabry Perot interferometer 27 is connected to a control device 28, which in the case of substantially constant wavelengths drives the detector 12 and triggers a recording of the laser radiation by the detector 12.

This therefore means that the apparatus 1 comprises a measuring device 27 which allows the time behavior of the wavelengths of the laser radiation of the laser emitters 2, 2a, 2b to be measured and that the measuring device is connected to a control device 28, which is suitable for driving the detector 12 in the case of substantially constant wavelengths and to trigger a recording of the interference patterns.

Optionally the apparatus 1 can have a regulating device 29, which regulates the laser emitters 2 as a function of the measurement results of the Fabry Perot interferometer 27 in such a manner that the wavelengths of the emitted laser radiation are substantially constant.

The interference patterns are recorded for each laser emitter 2 and therefore for each wavelength by the detector 12 and are analyzed and evaluated by means of a processing device 30. The processing device 30 transforms the interference pattern consisting of various spatial frequencies into the frequency domain which contains the 3D image information.

The evaluation of an interference pattern formed by reflection of the illuminating radiation 6 of a laser emitter 2 at an object point 16, 24, 26 and by interference with the appurtenant reference radiation 5 will be explained in detail hereafter.

If the object point 16, 26 is located at the focus $f_0$ or in the focal region of the lens 14, i.e., the object beam 21 after passage through the lens 14 is configured as a quasi-plane wave 23, preferably a Fourier transformation is used for the transformation into the frequency domain (frequency range). If the object point 24 is located outside the focal zone, i.e., the object beam 20 is configured as a slightly curved wave after passing the lens 14, a transformation into the frequency domain is preferably performed with the aid of a Fresnel transformation.

In the frequency domain, the evaluation of the interference pattern is made with regard to two aspects. On the one hand, the position of the object point 16, 24, 26 on the object 15 is determined with the assistance of the reference radiation 5 and therefore depending on the position of the laser emitter 2, whose laser radiation has resulted in the present interference pattern. On the other hand, depth information is determined for each object point 16, 24, 26. The term depth information is understood in the context of this disclosure as the position of the object point 16, 24, 26 in the depth, i.e., in FIG. 1a along the optic axis of the lens 14. It is used to identify elevations or recesses on the object 15.

The position of the object point 16, 24, 26 and the position of the respective laser emitter 2 is determined with the aid of the difference angle δ. Since the angle of incidence γ of the object beam and therefore also the difference angle δ depends on the position of the object point 16, 24, 26, different interference patterns of specific spatial frequencies characteristic of the position of the object point 16, 24, 26 are obtained as a function of the position of the object point 16, 24, 26. At the same time, the width of the frequency band in which fluctuations of the spatial frequency change as a function of the position of the object point 16, 24, 26 is narrowly limited for each laser emitter 2.

The difference angle δ is furthermore dependent on the position of the respective laser emitter 2 on the emitter chip 3. As has already been described further above, the reference radiation 5 of the respective laser emitter 2 impinges upon the detector 12 at different reference angles of incidence α depending on the position of the respective laser emitter 2. Consequently, each laser emitter 2 brings about a spatial frequency significantly different from, for example, the adjacent laser emitter 2. As a result of these significant differences of the spatial frequencies based on the position of the different laser emitters 2, the differences are not confused with variations based on different object points 16, 24, 26. Each laser emitter position allows a band of spatial frequencies which in turn can cover specifically the number of object points per emitter 2. For an adjacent emitter 2 there is then subsequently another band of spatial frequencies, etc. Therefore—after phase transformation (e.g., Fourier, Fresnel)—depth information can be assigned to a specific lateral object point 16, 24, 26 via the phase values of the local interference pattern.

If the information on the position of the object point 16, 24, 26 is now combined with the information on the respective laser emitter 2 and the depth information of the respective object point 16, 24, 26, a 3D structure of the object 15 can be determined.

In a real measurement, all the laser emitters 2 emit laser radiation simultaneously, whereby a plurality of interference patterns are formed on the detector surface 25. All the interference patterns are recorded by the detector 12 at the same time and evaluated by the processing device 30. The 3D structure of the object 15 is then generated based on these evaluations of all the interference patterns.

The apparatus 1 can preferably additionally measure layer thicknesses of layers (not shown), which are located on the object 15. If a layer is located on an object 15, as a result of the different wavelengths of the laser radiation emitted by the laser emitters 2, the illuminating beams 8a, 8b are partially reflected at the surface of the layer, whereas the other part of the illuminating beams 8a, 8b passes through the layer and are reflected at the surface of the object 15. Two slightly different sets of depth information for each object point 16, 24, 26 are available for the evaluation of the interference patterns in the frequency domain. The layer thickness can be determined by means of the different depth information. The apparatus 1 therefore comprises an inherent measuring unit for determining layer thicknesses, where the measuring unit can be configured as part of the processing device 30. The smallest layer thickness which can be measured with the apparatus 1 is given by the spectral width of the emitted wavelengths in the wavelength group.

Figure 1B:
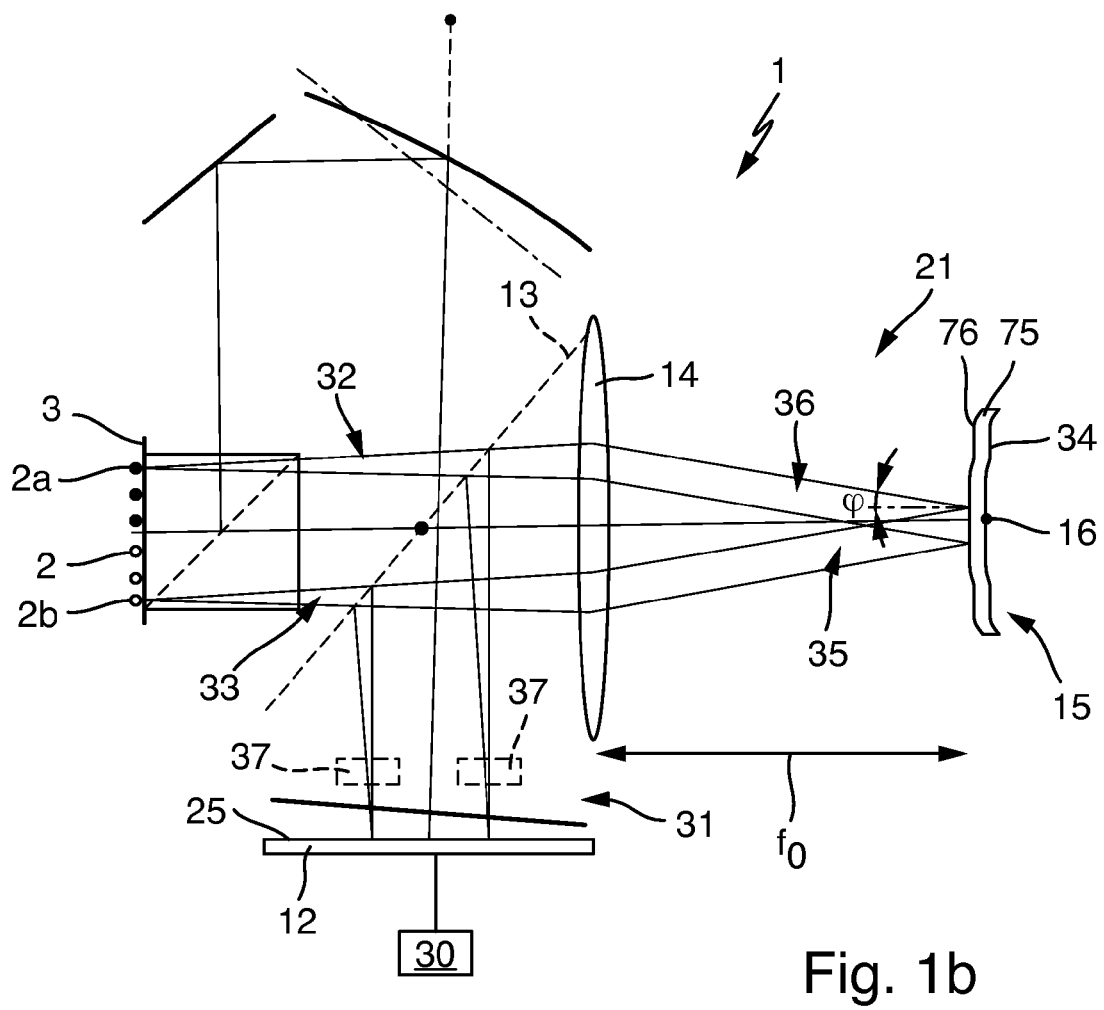
FIG. 1b shows in a schematic view the apparatus according to a second embodiment with a measuring unit which operates according to the principle of ellipsometry.

FIG. 1b shows a second embodiment of the apparatus 1. The apparatus 1 comprises a measuring unit 31 by which means the object radiation 21 of the laser emitters 2 reflected at a layer 75 to be measured, can be measured. In contrast to the apparatus 1 from FIG. 1a, the measuring unit 31 operates on the basis of the principle of ellipsometry and can thus determine the thickness of the layer 75 located on the object. The method of ellipsometry for determining layer thicknesses is known from the prior art.

The measuring unit 31 comprises the laser emitters 2. In contrast to FIG. 1a, the laser emitters in FIG. 1b are differently polarized. For example, the three upper laser emitters 2, 2a shown in FIG. 1b on the emitter chip 3 are polarized in a first type, e.g., P-polarized. The lower three laser emitters 2, 2b in FIG. 1b exhibit a second polarization, e.g., an S-polarization, which differs from the first polarization.

For example, a first illuminating beam 32 of the uppermost laser emitter 2a in FIG. 1b and a second illuminating beam 33 of the lowermost laser emitter 2b in FIG. 1b are shown on the emitter chip 3. The beam paths of the two illuminating beams 32, 33 will be explained in detail hereafter.

The illuminating beam 32 is transformed by the lens 14 into a plane wave and impinges upon the surface 76 of the layer 75 of the object 15 at an angle of incidence φ. Parts of the illuminating beam 32 are reflected at the surface 76 of the layer 75 as object radiation 21. Parts of the illuminating beam 33 pass through the layer 75 and are also reflected by a surface 34 of the object 15 on which the layer 75 is located, likewise as object radiation 21. The illuminating beam 33 reflected as object radiation 21 is shown in FIG. 1b as first object beam 35.

The first object beam 35 is reflected as a plane wave at the surface 34 and the surface 76 and after reflection again impinges upon the lens 14. This focuses the first object beam 35, which on its subsequent path is reflected at the second beam splitter 13 and impinges as a point beam upon the detector surface 25 of the detector 12. The detector 12 detects the object beam 35 which impinges upon it as a point beam.

A very smooth surface 76 of the layer 75 and a very smooth surface 34 of the object 15 at which the first illuminating beam 32 is reflected is assumed for the described beam path. With a slightly curved surface 76 or 34, the point beam directed onto the detector 12 would be broadened accordingly.

The second illuminating beam 33 runs as a mirror image to the first illuminating beam 32. The second illuminating beam 33 and the first object beam 35 are thereby at least partially superposed. The second illuminating beam 33 is reflected as second object beam 36 at the surfaces 76, 34, focused by the lens 14, and reflected by the second beam splitter 13 in such a manner that it impinges upon the detector surface 25 of the detector 12 as a point beam. The detector 12 detects the object beam 36, which impinges upon it as a point beam.

Based on the object beams 35, 36, the thickness of a layer 75 located on the object 15 can then be determined in a known manner with the aid of the processing device 30.

It is fundamentally also feasible that the layer 75 and the object 15 have rough surfaces 76, 34, which, as shown in FIG. 1a, reflect the object radiation 21 as a spherical wave. Such a method is also known from the prior art. In this case, each surface point (not shown) on the surface 76 of the layer 75 and each object point 16 of the object 15 is interpreted as a scattering point (cf. FIG. 1a). All the information of each surface point and object point 16, in contrast to the smooth surface, is thereby mapped onto the entire detector surface 25.

Optionally the apparatus 1 can comprise one or more analyzers, which are located between the second beam splitter 13 and the detector surface 25. The analyzers 37 are configured as polarizers, by which means the polarization state of laser radiation can be determined. If analyzers 37 are used, the laser emitters 2 emit laser radiation having a polarization angle of preferably 45 degrees so that the illuminating beams 32, 33 are emitted linearly polarized onto the layer 75 or the object 15. After reflection of the same at the layer 75 or the object 15, the object beams 35, 36 impinge upon the analyzers 37 located in a conjugated manner to the positions of the emitters 2a and 2b, which determine the polarization of the object beams 35, 36. For example, the laser radiation of the laser emitter 2a and the laser radiation of the laser emitter 2b are differently polarized by the layer thickness of the layer 75. The object beams 35, 36 are then incident on the detector 12, which detects these. In this context, located in a conjugated manner to the positions of the emitters 2a and 2b, means that the analyzers 37 are positioned according to the beam path of the laser radiation emitted by the laser emitters 2a, 2b.

It is further feasible to execute the lens 14 as two partial lenses, where each of the two illuminating beams 32, 33 is transmitted by respectively one of the two partial lenses. With the aid of additional mirrors (not shown), the illuminating beams 32, 33 are directed after the two partial lenses onto the layer 75 or the object 15. It is thus possible to achieve angles of incidence ϕ greater than or equal to 30 degrees, preferably close to 57 degrees. Layer thicknesses of less than 100 nm can also be measured thereby.

Figure 2:
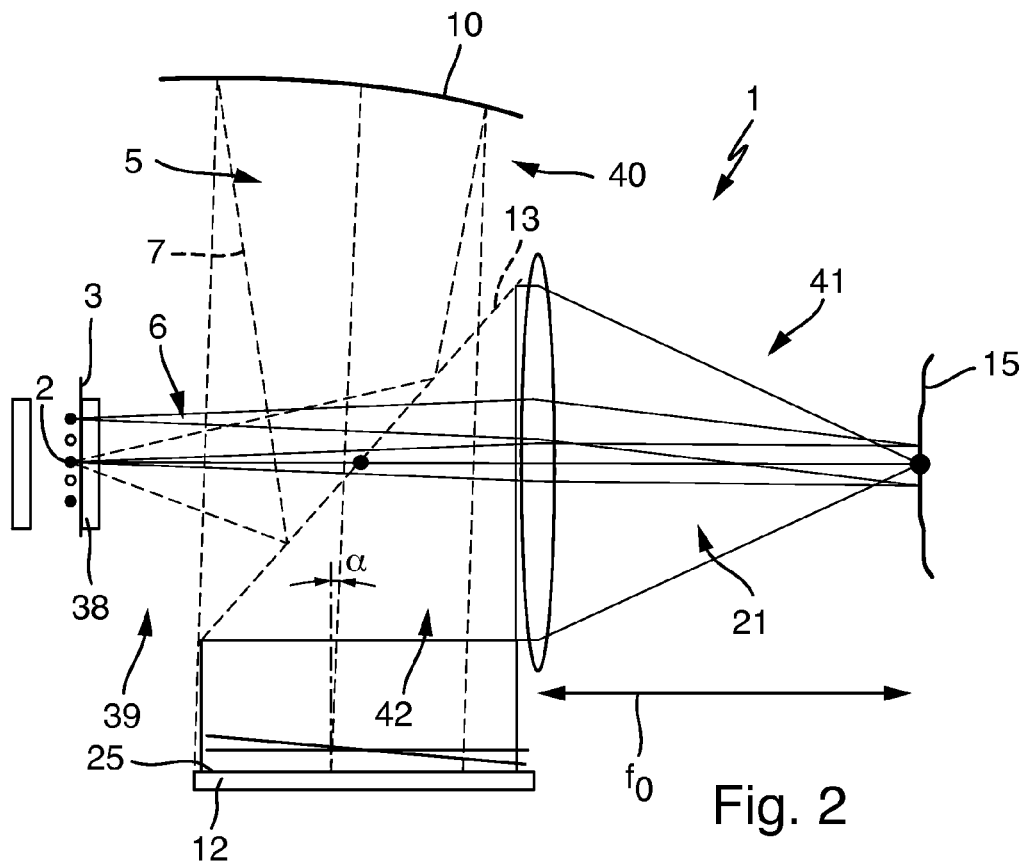
FIG. 2 shows schematically the apparatus according to a third embodiment in a Michelson setup.

FIG. 2 shows the apparatus 1 according to a third embodiment in a Michelson setup. This apparatus 1 differs from the apparatus 1 shown in FIG. 1a by an optical device configured as a micro-optic array 38. The micro-optic array 38 comprises the function of the first beam splitter 4 shown in FIG. 1a. Furthermore, with the aid of the micro-optic array 38, it is possible to differently polarize the reference radiation 5 and the illuminating radiation 6. The micro-optic array 38 splits the laser radiation of the laser emitters 2 into the reference radiation 5 and the illuminating radiation 6, where the reference radiation 5 has a significantly larger numerical aperture compared with the illuminating radiation 6.

Furthermore in the apparatus according to FIG. 2, compared to the apparatus 1 from FIG. 1a, the mirror 9 is dispensed with. The reference beam 7 of a laser emitter 2 is reflected at the beam splitter 13, which is configured as a beam splitter mirror, and is guided onto the parabolic mirror 10. This reflects the reference beam 7 in such a manner that it impinges upon the detector surface 25 of the detector 12 at a reference angle of incidence α.

It is also feasible to configure the beam splitter mirror 13 as a polarizing beam splitter, which reflects or transmits the laser radiation depending on the polarization states thereof. For example, the reference beam 5 is reflected and the illuminating radiation 6 is transmitted as a result of its different polarization state.

The reflection property of the parabolic mirror 10 in relation to the angle of incidence α can either be achieved, as shown in FIG. 2, by the parabolic mirror 10 being slightly inclined relative to the detector surface 25. However, it is also feasible not to incline the parabolic mirror 10 relative to the detector surface 25 and position the emitter chip 3 with the laser emitters 2 laterally so that the reference radiation 5 always impinges upon the detector 12 at a reference angle of incidence α which is different from zero. A lateral arrangement of the laser emitters 2 means in this context a displacement of the same in a vertical direction in FIG. 2 and/or a displacement transversely to the image plane in FIG. 2.

The parabolic mirror 10 can optionally have a circularly polarizing layer (not shown), which rotates the polarization state through 90° again in the direction of beam splitter 13 after passing through twice. This has the advantage that as much light as possible reaches the detector 12.

Apart from the differences described, the laser radiation of a laser emitter 2 runs as already described by reference to the apparatus 1 in FIG. 1a. The evaluation of the interference patterns on the detector 2 also takes place analogously to the apparatus 1 from FIG. 1a.

The beam splitter 13 defines in FIG. 2 four optical arms, which will be explained hereafter for a better understanding of the Michelson setup. The first optical arm is defined as illuminating arm 39, in which the emitter chip 3 with the laser emitters 2 and the micro-optic array 38 are located. In the illuminating arm 39 the illuminating radiation 6 runs in the direction of the beam splitter 13.

As second optical arm, the beam splitter 13 defines a reference arm 40, in which the reference radiation 5 reflected by the beam splitter 13, is deflected in the direction of the parabolic mirror 10 and from this back again in the direction of the beam splitter 13. The parabolic mirror 10 is preferably located in the reference arm 40.

The third optical arm is called object arm 41. The lens 14 and the object 15 are located therein. Optionally further lenses or optical elements can be located in the object arm 41. In the object arm 41 the illuminating radiation 6 is deflected onto the object 15 and the object radiation reflected by the object 15 is guided in the direction of the beam splitter 13.

The fourth optical arm is a detection arm 42. It is defined as the section from the beam splitter 13 to the detector 12. The detection arm 42 includes the detector 12 and optionally further beam splitters, e.g., if a plurality of detectors 12 are used.

Preferably optical polarization-rotating elements can be used in the object arm 41 and reference arm 40. In each case, with polarized illuminating and reference beams, it must be ensured that before the detector 12 an analyzer (polarizer, not shown) brings the light radiation back onto a common plane capable of interference. If no polarizing elements (including in the micro-optic array 38) are used, increased "crosstalk" (perturbing influences) must be expected between object radiation 21 and reference radiation 5, which must be corrected at some expense.

Figure 3:
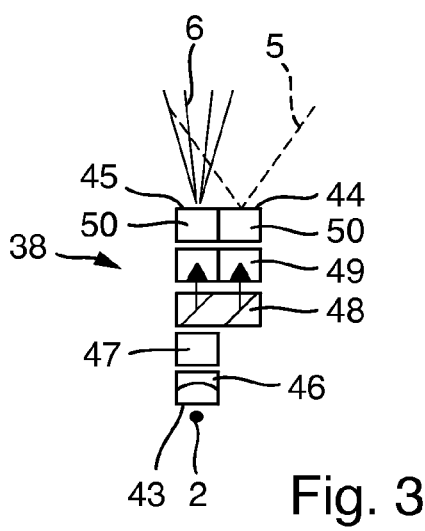
FIG. 3 shows a micro-optic array according to a first embodiment with a beam splitter in a side view.

FIG. 3 shows a detailed view of the micro-optic array 38 from FIG. 2 in a first embodiment from the side. The micro-optic array 38 can in principle not only be positioned in the Michelson setup according to FIG. 2 but also optionally in the Mach-Zehnder setup according to FIG. 1a between the laser emitters 2 and further optical devices of the apparatus 1 (FIG. 1a).

The laser radiation of each individual laser emitter 2 runs through the micro-optic array 38. As an example, the structure of the micro-optic array 38 is explained hereafter for a laser emitter 2. The structure of the micro-optic array 38 for the other laser emitters 2 is identical.

The micro-optic array 38 has an input 43, a first output 44, and a second output 45, via which the laser radiation leaves the micro-optic array 38 again.

After the laser radiation from the laser emitters 2 has been emitted via the input 43 into the micro-optic array 38, it runs through a rod-shaped cylindrical lens 46, which focuses the laser radiation in such a manner that an almost circular laser radiation having a numerical aperture of preferably about 0.1 is formed.

Located in the beam direction behind the cylindrical lens 46 is a polarizer 47, which polarizes the laser radiation in FIG.

3 perpendicular to the plane of the sheet. A beam splitter 48 then splits the laser radiation into the reference radiation 5 and the illuminating radiation 6. The reference radiation 5 thus formed then passes through a circulator 49, which rotates the plane of polarization by 90°, i.e., polarizes the reference radiation 5 parallel to the plane of the paper in FIG. 3. The illuminating radiation 6 on the other hand is not influenced in its polarization. Consequently the reference radiation 5 and the illuminating radiation 6 are polarized in different directions. Naturally, the polarization states can also be reversed, i.e., the laser radiation in FIG. 3 is polarized by means of the polarizer 47 parallel to the plane of the sheet whereas the reference radiation 5 is polarized by the circulator 49 perpendicular to the plane of the paper.

Both the reference radiation 5 and also the illuminating radiation 6 then each pass through a hologram 50, which provides the reference radiation 5 with a high numerical aperture and the illuminating radiation 6 with a low numerical aperture in comparison to this. The shape of the illuminating strip or strips can thereby be predefined.

After passing through the holograms 50, the reference radiation 5 and the illuminating radiation 6 emerge through the outputs 44 or 45 from the micro-optic array 38. However, it is also possible in principle to exchange the order of individual optical elements. It is also possible to provide a plurality of hologram planes.

Figure 4:
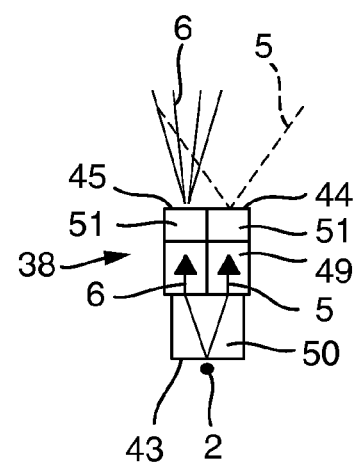
FIG. 4 shows the micro-optic array according to a second embodiment with a hologram in a side view.

FIG. 4 shows a micro-optic array 38 according to a second embodiment. The micro-optic array 38 constitutes a simplification compared with the micro-optic array 38 from FIG. 3. It differs in that the beam splitter 48 (FIG. 3) is formed as hologram 50 and the micro-optic array 38 furthermore only comprises a circulator 49 and a double polarizer 51.

Laser radiation of the laser emitter 2 enters into the micro-optic array 38 via the input 43. In the hologram 50 the laser radiation is initially split into reference radiation 5 and illuminating radiation 6. The reference radiation 5 is provided with a high numerical aperture in the hologram 50 and the illuminating radiation 6 is provided with a low numerical aperture in comparison to this. Analogously the shape of the illuminating strip or strips can be predefined.

In the following circulator 49, a polarization of the reference radiation 5 takes place, which is rotated in its polarization by 90 degrees. The illuminating radiation 6 on the other hand is not influenced in its polarization. Naturally this can also take place conversely. In the following double polarizer 51 both the reference radiation 5 and the illuminating radiation 6 are polarized. The direction of polarization of the illuminating radiation 6 differs as before by 90 degrees from the polarization of the reference radiation 5. Undesiredly rotated polarization fractions both in the reference radiation 5 and in the illuminating radiation 6 are jointly suppressed in the double polarizer 51.

The reference radiation 5 and the illuminating radiation 6 then emerge at the respective output 44, 45 from the micro-optic array 38. Here also in principle the order of the optical elements can be exchanged or the hologram 50 can be split into two single holograms with fewer individual tasks.

Figure 5:
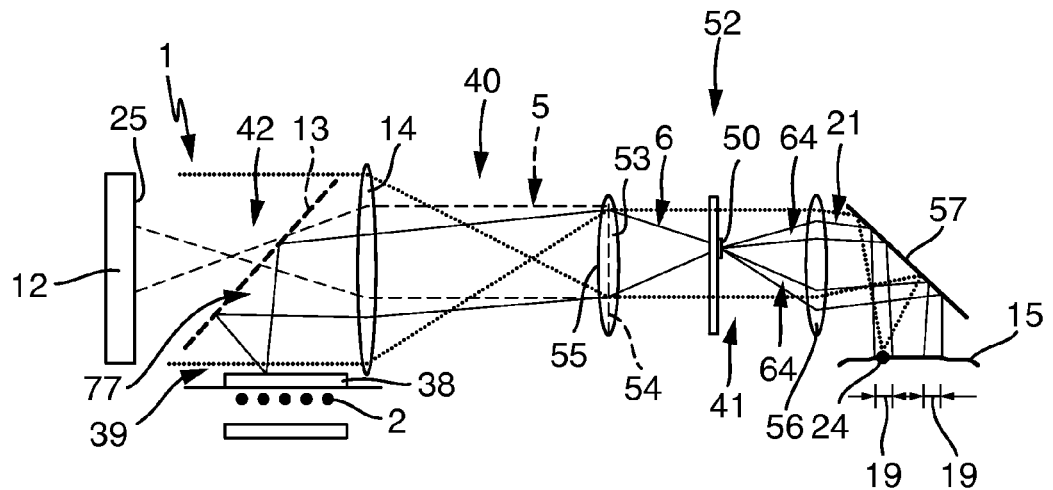
FIG. 5 shows the apparatus according to a fourth embodiment with a hologram for generating a plurality of illuminating strips in a schematic view.

FIG. 5 shows the apparatus 1 according to a fourth embodiment. Its structure corresponds to the Michelson setup from FIG. 2, where the positions of the laser emitters 2 and the detector 12 relative to the beam splitter 13 have been exchanged. Furthermore, the beam splitter 13 is designed as a polarizing beam splitter, i.e., it transmits or reflects radiation depending on the polarization.

In addition to the previously described apparatuses 1, the apparatus 1 according to FIG. 5 has an optics 52, which comprises a plurality of optical devices. The optics 52 extends from the lens 14 as far as the object-side end of the apparatus 1. One of the optical devices is configured as a second lens 53 with a back-reflector 54. Laser radiation impinging upon the back-reflector 54 is preferably 90% transmitted and 10% reflected. The back-reflector 54 together with the front-side curvature of the lens 53 thus takes over the function of the parabolic mirror 10 from FIG. 2.

Located on the front side 55 of the second lens 53 is a circular polarizer (not shown) with the aid of which reference radiation 5 impinging upon the lens 53 and the object radiation 21 is rotated through 90° in its polarization. It is thereby achieved that after transmission by the lens 14, the complete back-radiated laser radiation is transmitted to the polarizing beam splitter 13.

Another optical device of the optics 52 is configured as hologram 50, which deflects the illuminating radiation 6 of the laser emitters 2 in such a manner that this impinges upon the object 15 as illuminating strip 19. In particular, the numerical aperture of the illuminating radiation 6 of each laser emitter 2 is changed with the aid of the hologram 50 so that on the one hand, two mutually offset illuminating strips 19 are formed and on the other hand, each of these illuminating strips 19 has an approximately rectangular shape. By means of a third lens 56, which is also an optical device of the optics 52, the illuminating radiation 6 deflected by the hologram 50 is directed toward a mirror 57, which deflects the illuminating radiation 6 onto the object 15.

As a result of the different position of the laser emitters 2 and the detector 12 compared to FIG. 2, the positions of the illuminating arm 39 and the detection arm 42 were exchanged compared with FIG. 2. In contrast to the apparatus 1 from FIG. 2, in the apparatus according to FIG. 5 the reference arm 40 and the object arm 41 are at least partially superposed.

The path of the illuminating radiation 6 (shown as a continuous line) and the reference radiation 5 (shown as a dashed line) will be explained in detail as an example hereafter.

Laser radiation 77 emitted by the laser emitters 2 passes through the micro-optic array 38 and emerges from this again in a polarization state, i.e., polarized. No splitting of the laser radiation 77 into reference radiation 5 and illuminating radiation 6 takes place in the micro-optic array 38 (cf. FIG. 3).

The laser radiation 77 emerging from the micro-optic array 38 is linearly polarized in such a manner that the polarizing beam splitter 13 reflects the laser radiation 77 in the direction of the object 15 through the lens 14. The lens 14 transforms the laser radiation 77 into a plane wave. The laser radiation 77 is then incident on the second lens 53 and is circularly polarized in its plane of polarization by the circular polarizer on the front side 55 of the lens 53. The laser radiation 77 is further incident on the back-reflector 54, which reflects a small fraction, i.e., for example 10% thereof, back in the direction of the second beam splitter 13. This reflected fraction is again circularly polarized as a result of a renewed passage through the circulator on the front side 55 of the lens 53 so that its polarization state is effectively rotated by 90°. This means that the polarization state of the laser radiation 77 is rotated by 90° by passage twice through the circular polarizer.

The fraction reflected at the back-reflector 53 forms the reference radiation 5 and again impinges upon the second lens 14. The reference radiation 5 is then transmitted by the second beam splitter 13 as a result of the changed polarization. After the second beam splitter 13, the reference radiation 5 impinges upon the detector 12 and is recorded by this.

The fraction of the laser radiation 77 transmitted by the back-reflector 54 forms the illuminating radiation 6. The transmitted fraction is about 90% of the laser radiation 7. The back-reflector 54 is therefore configured as a beam splitter, which splits the laser radiation 77 into the reference radiation 5 and the illuminating radiation 6.

The illuminating radiation 6 is focused onto the hologram 50 with the aid of the second lens 53. The hologram 50 splits the illuminating radiation 6 into two beam bundles 64, which are deflected by the third lens 56 and the mirror 57 as two illuminating strips 19 onto the object 15.

The path of the illuminating radiation 6 reflected as object radiation 21 will be explained hereafter with reference to the object point 24. The object radiation 21 (shown as a dotted line) reflected from the object point 24—and circularly polarized by passing through the preceding circulator—impinges upon the mirror 57. This deflects the object radiation 21 onto the third lens 56, which transforms the object radiation 21 into a plane wave. The object radiation 21 then impinges upon the second lens 53 and thereby onto the circulator located on the front side, which polarizes the object radiation 21 according to the direction of passage of the polarizing beam splitter 13 now analogously to the reference radiation. The second lens 53 maps the object radiation 21 onto the lens 14, which projects this onto the second beam splitter 13. The beam splitter 13 transmits the object radiation 21 as a result of the corresponding polarization so that the object radiation 21 impinges upon the detector 12. The detector 12 records the object radiation 21.

At the detector 12, the reference radiation 5 and object radiation 21 interfere as described for FIG. 1a. The evaluation of the interference pattern produced hereby is performed analogously to the apparatus 1 from FIG. 1a. The illuminating strip 19 from which the object radiation 6 reflected by the object 15 originates can be determined with the aid of the angle of incidence γ and the difference angle δ (FIG. 1a) in the evaluation of the object radiation 21 on the detector surface 25 of the detector 12.

Figure 6:
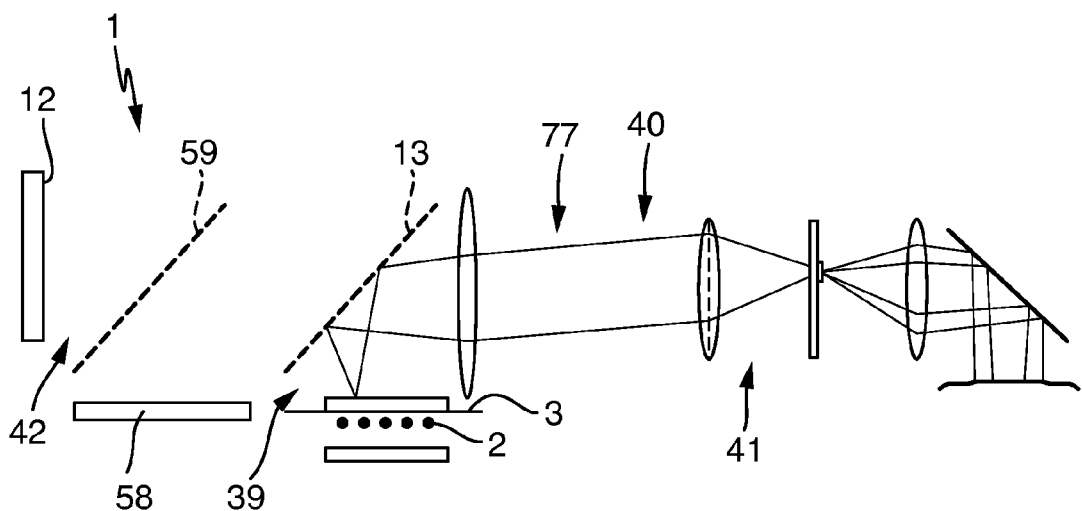
FIG. 6 shows the apparatus according to a fifth embodiment with two detectors in a schematic view.

The apparatus 1 according to a fifth embodiment shown in FIG. 6 differs from the apparatus 1 shown in FIG. 5 by a second detector 58 and an additional beam splitter 59, which deflects laser radiation onto the second detector 58. The apparatus 1 according to FIG. 6 has two emitter chips 3, where the front emitter chip 3 in FIG. 6 covers the rear emitter chip. The laser radiation of the emitter chips 2 located on the front emitter chip 3 in FIG. 6 impinges upon the detector 12. The laser radiation of the laser emitters located on the rear emitter chip in FIG. 6 impinges upon the second detector 58.

The laser emitters 2 of each emitter chip 3 form a wavelength group, where each wavelength groups can be assigned a central wavelength. The central wavelength is determined by forming the average over the different wavelengths of the laser radiation emitted by the laser emitters 2 of an emitter chip 3.

The additional beam splitter 59 splits the laser radiation of the laser emitters 2 incident upon it depending on the central wavelengths. This wavelength dependence of the additional beam splitter 59 is selected in such a manner that it transmits the laser radiation emitted by the laser emitters 2 of the front emitter chip 3 in FIG. 6, having a first central wavelength. The laser radiation of the laser emitters of the rear emitter chip not shown on the other hand is reflected with a second central wavelength at the additional beam splitter 59 onto the detector 58.

By using two emitter chips 3, the laser radiation 77 impinges upon the beam splitter 13 and the further optical devices of the apparatus 1 slightly inclined with respect to the plane of the sheet in FIG. 6.

When projected onto the plane of the sheet in FIG. 6, however, the path of the laser radiation 77 in the region of the illuminating arm 39, the reference arm 40, and the object arm 41 agrees with the path shown in FIG. 5. Differences in the beam path are only obtained in the detection arm 42 due to the additional beam splitter 59 as described above.

Figure 7:
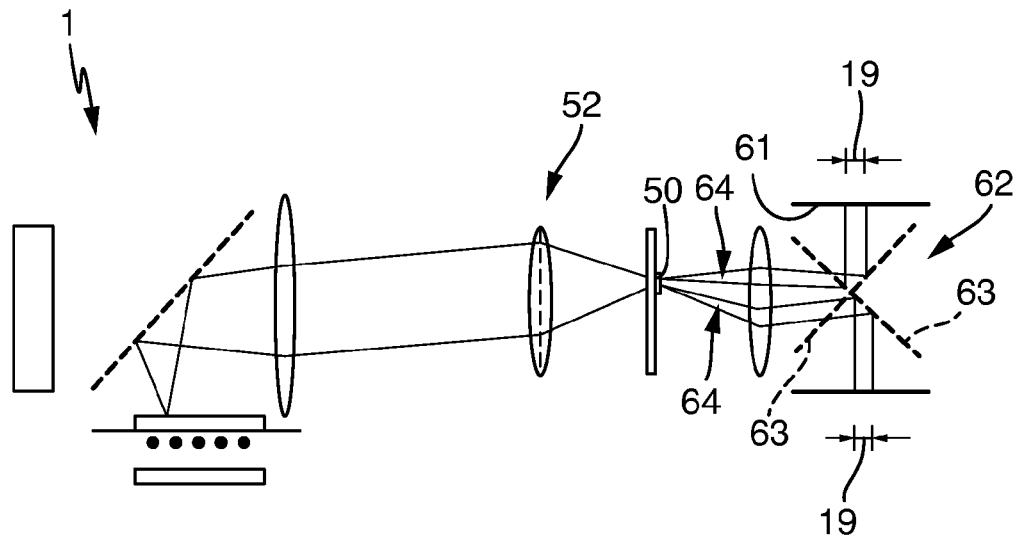
FIG. 7 shows the apparatus according to a sixth embodiment configured as an internal bore scanner in a schematic view.

FIG. 7 shows the apparatus 1 according to a sixth embodiment, which is configured as an inner bore scanner. This can be used to investigate an interior, in particular the interior of a bore 62 or an inner wall 61 of a bore 62. To this end the apparatus 1 has two beam splitters 63.

Analogously to the apparatus 1 from FIG. 5, the hologram 50 produces two beam bundles 64, which unlike the apparatus 1 from FIG. 5, are deflected with the aid of the beam splitter 63 in two opposite directions onto the inner wall 61 of the bore 62.

In order to investigate the bore 62 over its entire circumference, the optics 52 of the apparatus 1 is at least partially introduced into the bore 62. The optics 52 need not be positioned at the center of the bore 62. Possible centering errors can be compensated by two illuminating strips 19 impinging upon mutually opposite regions of the inner wall 61 of the bore 62. The optics 52 or the apparatus 1 is rotated in the interior of the bore 62 so that the bore 62 can be investigated over its entire circumference.

According to FIG. 7, the optics 52 of the apparatus 1 comprises, in addition to the components according to FIG. 5, the two beam splitters 63. The optics 52 according to FIG. 7 is configured in such a manner that it can be inserted into bore 62 having a diameter of, for example, 11 mm to 300 mm.

Figure 8:
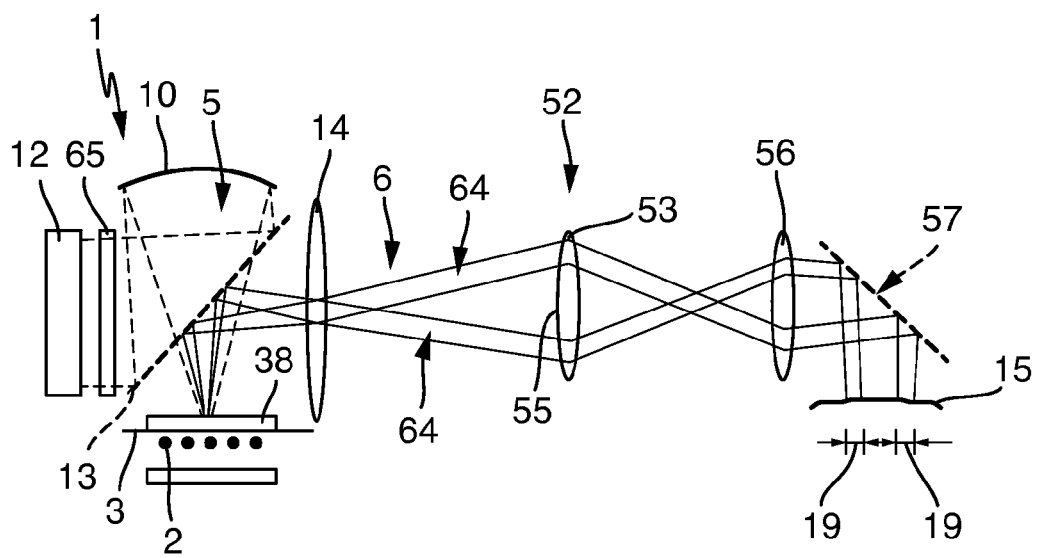
FIG. 8 shows the apparatus according to a seventh embodiment with a hologram in a micro-optic array in a schematic view.

FIG. 8 shows the apparatus 1 according to a seventh embodiment, which is based on the principle of the Michelson setup (FIG. 2). Compared to the apparatus 1 according to FIG. 5, a hologram is integrated in the micro-optic array 38, by which means two beam bundles 64 are formed, which are incident on the object as illuminating strips 19. The beam bundles 64 are deflected via the lenses 14, 53, 56 and the mirror 57 onto the object 15.

Furthermore, in contrast to the apparatus shown in FIG. 5, the micro-optic array 38 of the apparatus 1 splits the laser radiation of the laser emitters 2 into the reference radiation 5 and the illuminating radiation 6.

Furthermore, no back-reflector 54 (cf. FIG. 5) is integrated into the lens 53 but a parabolic mirror 10 is used in order to deflect the reference radiation 5 from the laser emitter 2 to the detector 12. The reference radiation 5 emerging from the micro-optic array 38 is reflected at the parabolic mirror 10 and is then reflected at the second beam splitter 13 in such a manner that it impinges upon an analyzer (polarizer) 65 and then on the detector 12. The parabolic mirror 10 is configured in such a manner that the reference radiation 5 according to the position of the laser emitter 2 on the emitter chip 3 impinges on the detector 12 at a certain reference angle of incidence α (cf. FIG. 1a).

Reference radiation 5 and illuminating radiation 6 leave the micro-optic array 38 with different polarization states. The second beam splitter 13 is configured as a polarization-sensitive beam splitter so that it transmits the reference radiation 5 having a first polarization and reflects the illuminating radiation 6 having a second polarization. This is naturally also feasible conversely.

The second lens 53 has a circulator (not shown) on its front side 55, which rotates the illuminating radiation 6 and thereafter the object radiation 21 (cf. FIG. 5) reflected by the object 15 by a total of 90° so that it is transmitted in the direction of the detector 12 by the second beam splitter 13 and is incident on the detector 12.

The analyzer (polarizer) 65 ensures that the interference pattern can be formed by identical polarization planes from the object beam 21 and the reference beam 5.

Figure 9:
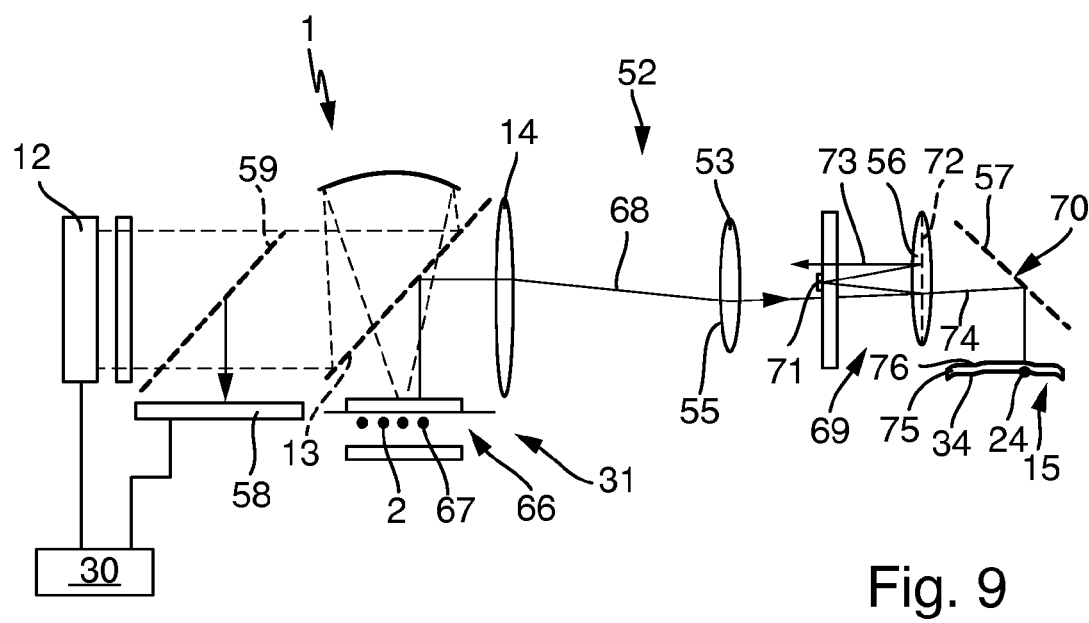
FIG. 9 shows the apparatus according to an eighth embodiment with a measuring unit which operates according to the principle of white light interferometry in a schematic view.

FIG. 9 shows the apparatus 1 according to an eighth embodiment, which differs from the embodiment according to FIG. 8 by a measuring unit 31 to measure the thickness of a layer 75 located on the object 15. The measuring unit 31 comprises a white light point sensor 66, which operates according to the known principle of interferometry.

The white light point sensor 66 comprises as light source 67 a broad-spectrum point light source, preferably having a spectrum width of 10 nm to 100 nm. The light source 67 emits around a central wavelength of preferably 1300 nm, which penetrates through scattering media (e.g., tissue) very well. The light radiation of the light source 67 is shown, for example, by the light beam 68.

Part of the white light point sensor 66 is further a second detector 58, which detects the light radiation of the light source 67. In order to deflect the light radiation to this second detector 58, the apparatus 1 has an additional beam splitter 59, which reflects or transmits radiation depending on the wavelength.

For the layer thickness measurement based on the method of interferometry, the apparatus 1 further has a second reference arm 69 and a second object arm 70. The second reference arm 69 is defined as twice the distance between a reference mirror 71 located in the optics 52 of the apparatus 1 and a semitransmitting mirror 72 in the third lens 56. The second object arm 70 is defined as the distance between the semitransmitting mirror 72 and an object point 24 of the object 15. Apart from path differences of 0.1 mm to a maximum of, for example, 3 mm, reference arm 69 and object arm 70 are certainly not completely identical provided that the apparatus 1 is located at a corresponding distance from the object 15.

The optical path of the white light point sensor 66 is explained hereafter. For its function it is known according to the prior art that, by means of tunable wavelength, the layer thickness information can be obtained by means of the frequency measurement at a detector 58. For this purpose the path difference between object arm 70 and reference arm 69 must be different from zero.

The light source 67 of the white light point sensor 66 emits a light beam 68, which is deflected by means of the beam splitter 13, through the lens 14 and the second lens 53 past the reference mirror 71 onto the semitransmitting mirror 72. The semitransmitting mirror 72 splits the light beam 68 into a reference beam 73, which is reflected, and an illuminating beam 74, which is transmitted.

The reference beam 73 reflected at the semitransmitting mirror 72 impinges upon the reference mirror 71, is reflected from this onto the semitransmitting mirror 72, and reflected again in the direction of the second beam splitter 13. It is also feasible to configure the reference mirror 71 as a hologram, which reflects the reference beam 73 onto the semitransmitting mirror 72 which is sensitive to the wavelength of the white light point sensor 66.

The illuminating beam 74 transmitted by the semitransmitting mirror 72 is deflected via the mirror 57 onto the object 15. The illuminating beam 74 passes through a layer 75 located on the object 15 and impinges inter alia upon the object point 24 of the object 15. The path of the illuminating beam 74 reflected at the object point 24 as object beam (not shown) is accomplished analogously to the object radiation 21 reflected at the object 15 in FIG. 8. However, the object beam according to the eighth embodiment of the apparatus 1 is reflected by the additional beam splitter 59 as a result of its wavelength and deflected onto the detector 58.

With the aid of the reference radiation 5 and illuminating radiation 6 emitted by the laser emitters 2 (cf. FIG. 8), the apparatus 1, analogously to the apparatus 1 from FIG. 8, is able to detect a surface 76 of the layer 75. The measuring unit 31 additionally enables the object 15 below the layer 75 to be scanned. Since both the surface 76 and also the object 15 below the layer 75 can be determined, the layer thickness of the layer 75 can be calculated with the aid of the processing device 30.

The embodiments of the apparatus 1 shown in FIGS. 5 to 9 can be used as dental scanners for example for the three-dimensional detection of a tooth or entire jaw. For this purpose the optics 52 preferably has a diameter of at most 20 mm, preferably of at most 10 mm. The optics 52 has a length of at most 150 mm, preferably of at most 100 mm. The length of the optics 52 is defined as the distance between the lens 14 and the object-side end of the apparatus 1.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. Apparatus for detecting a 3D structure of an object, comprising:
   a first laser emitter which generates laser radiation having a first wavelength and a second laser emitter which generates laser radiation having a second wavelength different than the first wavelength, wherein the first and second lasers are positioned such that the illuminating radiation of the first laser emitter and the illuminating radiation of the second laser emitter impinge upon the object at different angles of incidence;
   optical devices, including a beam splitter which splits the laser radiation from each of the first and second laser emitters into reference radiation and illuminating radiation, wherein the illuminating radiation impinges upon the object to be measured, is reflected by the object as object radiation, and interferes with the reference radiation to form interference patterns;
   a detector which records the interference patterns; and
   a measuring device which measures the two wavelengths of the laser radiation of the laser emitters and influences the recording of the interference patterns.

2. The apparatus according to claim 1, wherein the measuring device measures the time behavior of the wavelengths of the laser radiation of the laser emitters, the apparatus further comprising a control device that actuates the detector in the event of substantially constant wavelengths and triggers a recording of the interference patterns.

3. The apparatus according to claim 2, further comprising a regulating device which, as a function of the measurement results of the measuring device, regulates the laser emitters such that the wavelengths of the emitted laser radiation are substantially constant.

4. The apparatus according to claim 2, wherein the measuring device comprises a Fabry Perot interferometer.

5. The apparatus according to claim 1, wherein the first laser emitter and the second laser emitter are located on a common emitter chip and spaced apart from one another.

6. The apparatus according to claim 1, wherein at least one of the optical devices is configured to reflect the reference radiation such that the reference radiation of the individual laser emitters is incident on the detector at different reference angles of incidence.

7. The apparatus according to claim 1, wherein at least one of the optical devices is a hologram which deflects the illuminating radiation in such a manner that it impinges upon the object as one or more illuminating strips.

8. The apparatus according to claim 1, wherein a micro-optic array comprises the beam splitter which splits the laser radiation of the laser emitters into the reference radiation and the illuminating radiation and supplies both sets of radiation with different radiation profiles.

9. The apparatus according to claim 8, wherein the micro-optic array comprises at least one polarizer configured to polarize the illuminating radiation.

10. The apparatus according to claim 8, wherein the micro-optic array comprises at least one polarizer configured to polarize the reference radiation of the laser emitters.

11. The apparatus according to claim 8, wherein the micro-optic array comprises at least one hologram.

12. The apparatus according to claim 1, wherein at least one of the optical devices is configured as a chromatically dispersive lens or as a chromatically dispersive minor.

13. The apparatus according to claim 1, further comprising two emitter chips and wherein the detector comprises two detectors, wherein the laser radiation of the laser emitters located on one of the two emitter chips impinges upon the one detector and the laser radiation of the laser emitters located on the other of the two emitter chips impinges upon the other detector.

14. The apparatus according to claim 1, further comprising a measuring unit configured to measure the thickness of a layer located on the object.

15. The apparatus according to claim 14, wherein the measuring unit comprises a white light point sensor, which operates according to the principle of frequency-scanning interferometry.

16. The apparatus according to claim 14, wherein the measuring unit is configured to determine the thickness of the layer located on the object based on the principle of ellipsometry.

17. The apparatus according to claim 1, further comprising optics configured to be inserted into the inner mouth region of a patient or into a bore.

18. Apparatus for detecting a 3D structure of an object, comprising:
- a first laser emitter which generates laser radiation having a first wavelength and a second laser emitter which generates laser radiation having a second wavelength different than the first wavelength, wherein the first and second lasers are positioned such that the illuminating radiation of the first laser emitter and the illuminating radiation of the second laser emitter impinge upon the object at different angles of incidence;
- optical devices, including a beam splitter which splits the laser radiation from each of the first and second laser emitters into reference radiation and illuminating radiation, wherein the illuminating radiation impinges upon the object to be measured, is reflected by the object as object radiation, and interferes with the reference radiation to form interference patterns;
- a detector which records the interference patterns; and
- a measuring device which measures the two wavelengths of the laser radiation of the laser emitters and influences the recording of the interference patterns;
- wherein the first laser emitter and the second laser emitter are located on a common emitter chip and spaced apart from one another.

* * * * *